United States Patent [19]

Bass et al.

[11] Patent Number: 5,306,734
[45] Date of Patent: Apr. 26, 1994

[54] USE OF VISCOSITY AS AN IN-LINE DIAGNOSTIC FOR HIGH INTERNAL PHASE EMULSION GENERATION

[75] Inventors: Ronald M. Bass; Thomas F. Brownscombe, both of Houston, Tex.

[73] Assignee: Shell Oil Company, Houston, Tex.

[21] Appl. No.: 118,541

[22] Filed: Sep. 8, 1993

[51] Int. Cl.$^5$ ............................................... C08J 9/28
[52] U.S. Cl. ....................................... 521/63; 521/61; 521/64; 521/917
[58] Field of Search ..................... 521/61, 64, 917, 63

[56] References Cited

U.S. PATENT DOCUMENTS

| | | | |
|---|---|---|---|
| 3,565,817 | 2/1971 | Lissant | 252/312 |
| 4,522,953 | 6/1985 | Barby et al. | 521/64 |
| 4,788,225 | 11/1988 | Edwards et al. | 521/147 |
| 5,149,720 | 9/1992 | DesMarais et al. | 521/63 |
| 5,189,070 | 2/1993 | Brownscombe et al. | 521/64 |
| 5,200,433 | 4/1993 | Beshouri | 521/64 |
| 5,210,104 | 5/1993 | Bass et al. | 521/64 |

FOREIGN PATENT DOCUMENTS

| | | |
|---|---|---|
| 0060138A1 | 9/1982 | European Pat. Off. |
| 0299762A2 | 1/1989 | European Pat. Off. |
| 2194166A | 3/1988 | United Kingdom |

OTHER PUBLICATIONS

Seiscor Technologies, Inc., Flow Characterization Rheometer (FCR), Product Bulletin.
R. B. Bird, R. C. Armstrong, O. Hassager, Dynamics of Polymeric Liquids, Fluids Mechanics, Second Edition, vol. 1, pp. 175–178, Wiley, NY.
I. M. Krieger, Shear Rate In The Couette Viscometer, Transactions of the Society of Rheology 12:1, 5∝11 (1968).
W. H. Geidt, Ph.D., Viscosity Measurements, Principles of Engineering Heat Transfer, 6.4, pp. 99–100, Van Nostrand, NY (1957).
H. M. Princen and A. D. Kiss, Rheology of Foams and Highly Concentrated Emulsions—IV. An Experimental Study of the Shear Viscosity and Yield Stress of Concentrated Emulsions, Journal of Colloid and Interfaces Science, vol. 128, No. 1, Mar. 1, 1989, pp. 176–187.
Rosemount, Inc., Model 1151 DP/GP and Model 1144G Pressure and Differential Pressure Transmitters with Model 1199 Remote Diaphragm Seals, Product Bulletin.

*Primary Examiner*—Morton Foelak

[57] ABSTRACT

A lightweight absorbent foam is produced using a high internal phase emulsion (HIPE), the production of which incorporates the use of capillary viscosity measurements as an in-line diagnostic for HIPE quality. The in-line diagnostics yield measurements of viscosity slope and amplitude. These measurements offer several advantages for monitoring emulsion quality, including stable high resolution measurement of hardware-independent parameters of the whole flow, without the need for sampling.

10 Claims, 7 Drawing Sheets

SWEAT INDICATION IN A CAPILLARY

*FIG.13*

USE OF VISCOSITY AS AN IN-LINE DIAGNOSTIC FOR HIGH INTERNAL PHASE EMULSION GENERATION

FIELD OF THE INVENTION

The invention is directed to a lightweight (low density) absorbent foam, which is produced by using a high internal phase emulsion (HIPE). The continuous phase is a curable monomer mixture plus surfactant, and the dispersed phase is water with salt. An initiator is also present in the continuous phase and/or dispersed phase. The invention is more particularly directed to the use of capillary viscosity measurements as an in-line diagnostic for HIPE quality.

BACKGROUND OF THE INVENTION

Water-in-oil emulsions having a relatively high ratio of water phase to oil phase are known in the art as high internal phase emulsions ("HIPEs" or "HIPE" emulsions). Continuous processes for preparing HIPE emulsions are disclosed, for example, in Lissant, U.S. Pat. No. 3,565,817, issued Feb. 23, 1971 and Bradley et al, British Patent Application 2194166A, published Mar. 2, 1988.

The prior art has also recognized that the nature and characteristics of the porous polymeric foam materials formed by polymerizing HIPE emulsions is very much dependent on both the type of components which make up the polymerizable HIPE emulsion and the process conditions used to form the emulsion. For example, Unilever, European patent Application No. 60138, published Sep. 15, 1982 discloses a process for preparing absorbent porous polymers (i.e., foams) from high internal phase emulsions comprising at least 90% by weight of water with the oil phase containing polymerizable monomers, surfactant and a polymerization catalyst. Edwards et al, U.S. Pat. No. 4,788,225, issued Nov. 29, 1988 discloses the preparation of porous polymer materials which are rendered elastic by selecting certain monomer types (styrene, alkyl(meth)acrylates, crosslinker) and by using certain processing conditions to control the cell size of the eventually resulting porous polymer. Unilever, European Patent Application EP-A-299,762, published Jan. 18, 1989 discloses that the use of an electrolyte in the water phase of polymerizable HIPE emulsions can affect the size of the openings between cells of the eventually resulting porous polymeric foam material.

Notwithstanding the fact that the existence and synthesis of polymerizable HIPE emulsions is known in the art, preparation of HIPE emulsion suitable for polymerization to useful absorbent foam material is not without its difficulties. Such HIPE emulsions, and especially HIPE emulsions having a very high ratio of water phase to oil phase, tend to be unstable. Very slight variations in monomer/crosslinker content in the emulsion, emulsifier selection, emulsion component concentrations, and temperature and/or agitation conditions can cause such emulsions to "break" or to separate to at least some degree into their distinct water and oil phases. Even if stable emulsions can be realized, alterations in emulsion composition and processing conditions can significantly affect the properties and characteristics of the eventually realized polymeric foam materials, thereby rendering such foam materials either more or less useful for their intended purpose. Such HIPE emulsion preparation difficulties can become even more troublesome when there is a need to produce polymerizable emulsions via a continuous process on an industrial or pilot plant scale in order to provide commercially useful or development quantities of polymeric absorbent foam materials.

In present processes, HIPE is sampled from the process stream and viscosity is measured in a bench top couette viscometer.

It is, therefore, highly desirable to measure (or calculate) HIPE qualities in-line, i.e. without the need for sampling, whereby the whole fluid can be measured.

Applicant has found that viscosity is a useful process indicator of emulsion quality for the following reasons:

(1) Viscosity is highly sensitive to changes in the emulsion due to variations in process and formulation parameters.

(2) Viscosity is an intrinsic property of the emulsion that is independent of mixer hardware, so the data can be compared for different mixing systems.

(3) Viscosity can detect the presence of sweat (small amounts of free water) with high sensitivity.

(4) Viscosity provides immediate feedback whereas 24 hours or more may elapse before properties of the finished product can be measured.

SUMMARY OF THE INVENTION

Applicant has devised a process whereby qualities of the whole fluid can be measured (or calculated), in-line without sampling, using precise commercial process instrumentation.

Oil and water phases are injected into a pin mill mixer to produce an emulsion having a high water-to-oil phase ratio. The emulsion is forced through in-line tubes having different cross-sectional areas. Pressure drops are taken across sections of the tubing, and with the known flow rate, properties of the emulsion can be determined.

Because the emulsion is a power law fluid, viscosity can give two fluid parameters (magnitude and slope). These parameters have been observed to vary independently so both are needed to characterize the emulsion.

Mixer head pressure or pressure drop in a single capillary have also proven to be useful indicators of emulsion quality. However, due to variable buildup of emulsion in the mix head, it is possible that head pressure can vary when the emulsion is not changing. Consequently, a pressure measurement downstream of the mix head, whether with one capillary or two, may be preferable to head pressure as an emulsion quality indicator. A divergent trend between head pressure and downstream measurements is also a good indication that the mix head may be fouling.

In-line diagnostics to measure emulsion quality, such as viscosity, may be useful for controlling temperature, feed rates, and mill RPM, and to diagnose equipment or formulation problems.

DETAILED DESCRIPTION OF THE INVENTION

In batch processes, HIPEs are commonly produced by starting with a pure continuous phase and slowly stirring in the dispersed phase until the desired phase ratio is achieved.

The formulation used by Applicant is an oil-continuous emulsion. In a standard formulation used in formulating HIPEs shown in the Figures, the oil phase consists of a mixture of curable monomers (20 percent styrene, 20 percent divinylbenzene, 60 percent ethyl hexyl acrylate) and surfactant (12 weight percent Span 20 basis the monomers). The initiator is a persulfate salt. The water phase also has a high electrolyte content (typically 10 percent calcium chloride). The water/oil weight ratios are commonly in the range of 25/1 to 50/1. The desired water/oil volume ratio is on the order of 40/1. The emulsion is cured, sliced into layers and squeezed dry. Typically the layers stay thin until they are wetted. Other suitable formulations for HIPEs are described in Assignee's U.S. Pat. Nos. 5,189,070, issued Feb. 23, 1993; 5,200,433, issued Apr. 6, 1993; and 5,210,104, issued May 11, 1993, the disclosures of which are incorporated herein by reference.

The mixture of polymerizable monomers contains one or more vinyl monomers and a crosslinker. The surfactant can be added to the water phase and/or the oil phase and the polymerization catalyst can be added to at least a portion of the oil phase, water phase or emulsion.

DESCRIPTION OF THE MIXER

Figure 7:
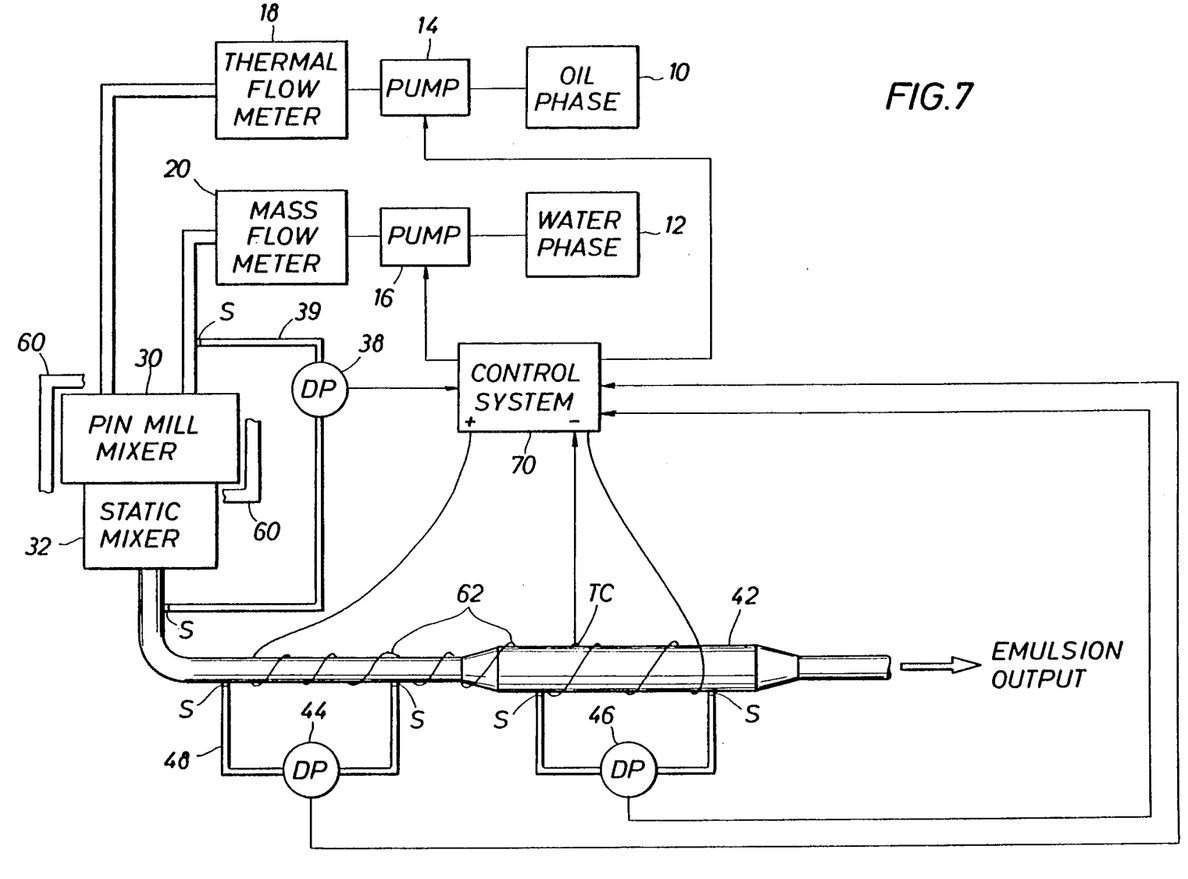
FIG. 7 is a schematic configuration for an in-line process viscometer for a power law fluid.

Referring to FIG. 7, the mixing system is a pin mill, designed for polyurethane production, such as those manufactured by Edge-Sweets Corporation. A size #2 head was used for the work described herein. The pin mill consists of a cylindrical steel impeller in a vertical cylindrical steel barrel. Cylindrical pins extend from the impeller body to just inside the barrel wall. The water and oil phases are injected at the top of the mill and emulsion is discharged from the bottom. The barrel tapers to a cone below the impeller. A static mixer is mounted below the barrel cone to provide back pressure during startup but is not believed to contribute to the emulsification process. The emulsion is commonly mixed at about 45° C. Emulsion is poured into a small polypropylene tub, which is cured as a "bun".

The inside diameter of the barrel is one inch. The standard impeller is 3.75 inches long. The diameter of the impeller shaft is 0.50 inches. The diameter of the pins is 0.187 inches and the pin length is 0.25 inches. There are a total of 40 pins on the standard impeller. The pins are arrayed in six vertical rows; four of 7 pins and two of six pins. The gap between the standard impeller pins and the inside barrel surface is 0.02". The mixer can run as high as 4000 RPM.

The two liquid phases are injected with gear pumps into the pin mill through small diameter tubes ("orifices") that extend down to just above the impeller. The maximum total flow rate is about 2 lb/min. The water phase is metered by a mass flow meter. The oil phase is metered by a thermal flow meter. The flow rates are determined by setting RPM levels on the pumps. All data values are recorded automatically in real time by a monitoring and control system and flow rates are automatically adjusted to achieve desired emulsion qualities.

Sweating

If emulsification is incomplete due to inadequate residence time in the mixer, or if coalescence is produced by excessive shearing, free water is observed as "sweat" (small water droplets) on the exterior of the "tube" of emulsion that is discharged from the static mixer. According to the Helmholtz principle of minimum energy dissipation, the velocity profile in steady flow must be such as to minimize the total rate of energy dissipation in the fluid. This means that low viscosity fluids are located in the high shear regions. Consequently, excess water tends to flow along the walls of the mixer or tubing, greatly reducing the pressure drop compared to emulsion flow with no free water present. This effect is manifested as a reduction in head pressure or in pressure drop in tubing, and can cause a slip layer to occur in a couette viscometer. Sweat is associated with large "defects" in the foam, which cause undesirable performance properties.

Dependence of Emulsion and Foam Properties on Mixing Conditions

Figure 1:
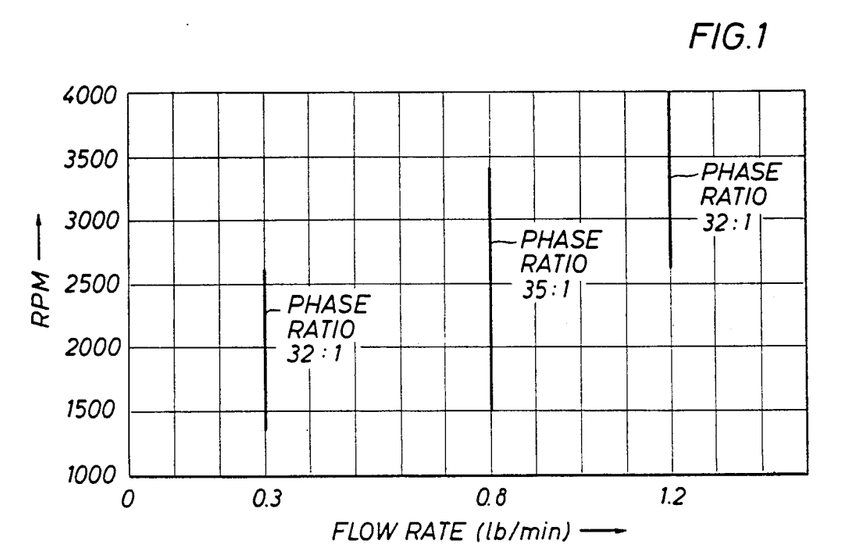
FIG. 1 is an example of an RPM operating window.
Figure 2:
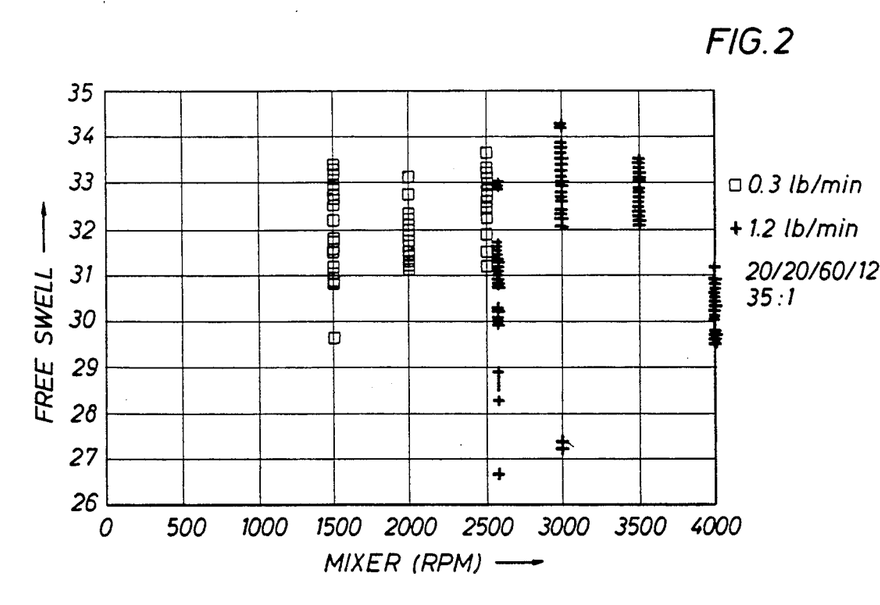
FIG. 2 is an example of variability of emulsion properties with mixing conditions.

A set of properties has been defined to characterize the behavior of the cured foam, including dry thickness, absorbency (free swell), wicking rate (VWR), and fluid retention under load (RTCD). Definitions and testing procedures are as stated in Assignee's U.S. Pat. No. 5,189,070 the disclosure of which is incorporated herein by reference. Drop size can be measured qualitatively with scanning electron micrographs of the cured, dried foam. The other properties are strongly dependent on drop size, which in turn depends on mixing conditions and the formulation. If the flow rate is too high or the mixer RPM is too low, the residence time is inadequate. In this case, a wide standard deviation of measured property values may be observed, and the emulsion may "sweat", as described above. If the RPM is too high, coalescence may result, with the same consequences. The range of RPM's over which a sweat-free emulsion can be produced at a given flow rate and temperature is called the RPM "operating window". The operating window is a function of the formulation, phase ratio, flow rate, mix head design, and mixing temperature. As the flow rate, temperature or water/oil phase ratio are increased, the operating window narrows until there is only a very small range of RPM over which sweat-free emulsion can be produced. This sets an upper limit, for example on the flow rate through the mixer. Within the operating window, an increase in RPM results in a decrease in drop size and an increase in emulsion viscosity. FIG. 1 shows an example of characterization of an RPM operating window for a water/oil ratio of 32/1 and 35/1. FIG. 2 shows an example of property variations (free swell) with operating conditions for 24 samples taken from buns produced at two different flow rates. Each vertical line represents 24 data points. At 2500 RPM, the high flow rate data is offset to the right of the low flow rate data for clarity. At the low flow rate (0.3 lb/min.), the properties show a mild trend with RPM but the standard deviation is nearly independent of RPM because of the relatively long residence time. At the high flow rate (1.2 lb/min.), however, the standard deviation is highly sensitive to RPM due to the much shorter residence time, and due to coalescence at the highest RPM. Scanning electron micrographs show clearly that drop size decreases with RPM, all other factors being held constant, due to higher shear. Drop size also increases with flow rate, all other factors being held constant, due to lower residence time. The most desirable properties are achieved at higher mixer RPM. This currently appears to be due to the smaller cell size achieved at high mixing intensity.

Viscoelastic Model of HIPE

In the description and analysis that follow, the following definitions apply:

$\tau$ = shear stress, Pascals
$\dot{\gamma}$ = shear rate, sec$^{-1}$
$\tau_0$ = yield stress, Pascals
$\mu_0$ = emulsion viscosity at a shear of 1/sec, Pascal-sec
$\mu_e$ = emulsion viscosity, Pascal-sec
n = power law exponent, dimensionless
$\sigma$ = interfacial tension, Newton/meter
$\phi$ = volume fraction of dispersed phase, dimensionless
$D_{32}$ = Sauter mean diameter, meters
$\mu_c$ = viscosity of the continuous phase, Pascal-sec
$Q_e$ = emulsion volume flow rate, meter$^3$/sec
$R_c$ = radius of couette cup, meters
$R_b$ = radius of couette spindle, meters
$\Omega$ = angular velocity of couette, sec$^{-1}$
r = radius of emulsion flow in capillary, meters
$u_w(r)$ = water film velocity at r, meters/sec
$u_e(r)$ = emulsion velocity at r, meters/sec
g = thickness of lubricating layer in lubricated capillary flow, meters
R = capillary radius, meters
E = elastic modulus, Pascals
G = shear modulus, Pascals
A = area, meter$^2$
d = capillary diameter, meters
$\mu_w$ = water viscosity, Pascal-sec dp/dL = pressure drop per unit length in capillary, Pascal/meter

Theoretical HIPE Model

Princen et. al. (Princen, H. M., Kiss, A. D., "Rheology of Foams and Highly Concentrated Emulsion", Journal of Colloid and Interface Science, Vol. 128, No. 1, Mar. 1, 1989) have investigated theoretical models of HIPE viscoelastic properties. Princen uses a two dimensional monodisperse model of HIPE. Based on both his model and experimental results, Princen finds HIPE to be a power law fluid with a yield stress, as follows;

$$\text{emulsion viscosity, } \mu_e = \frac{\tau_0}{\dot{\gamma}} + \frac{\mu_0}{\dot{\gamma}^{\frac{1}{2}}} \text{ Pascal-sec} \quad (1)$$

emulsion viscosity at a shear of 1 Pascal-sec, $$\mu_0 = 32(\phi - 0.73)\left(\frac{2\sigma\mu_c}{D_{32}}\right) \text{Pascal-sec} \quad (2)$$

The corresponding static shear modulus is given by Princen as $$\text{shear modulus, } G = 1.77 \frac{\sigma}{R_{32}} \phi^{\frac{1}{3}}(\phi - 0.73) \text{ Pascals} \quad (3)$$

The Princen model assumes a large excess of surfactant in the continuous phase. This results in a constant viscosity slope of about ½. However, with many surfactant systems, much lower slopes have been observed (as low as 0.2). This is probably due to surfactant depletion, which is more pronounced for "good" emulsifier systems. The elastic modulus of a film is given by $$\text{elastic modulus, } E = \frac{d\sigma}{d(\ln A)} \text{ Pascals} \quad (4)$$

When a drop is deformed, its surface area increase. When the surfactant becomes depleted, the interfacial tension rises sharply when more surface area is created, resulting in a high elastic modulus. The drops therefore become difficult to deform, reducing the observed shear thinning, which in turn produces a lower measured viscosity slope. In addition, real emulsions are generally polydisperse, so their behavior can be expected to deviate from this model.

Viscoelastic Behavior of the Emulsion

Figure 3:
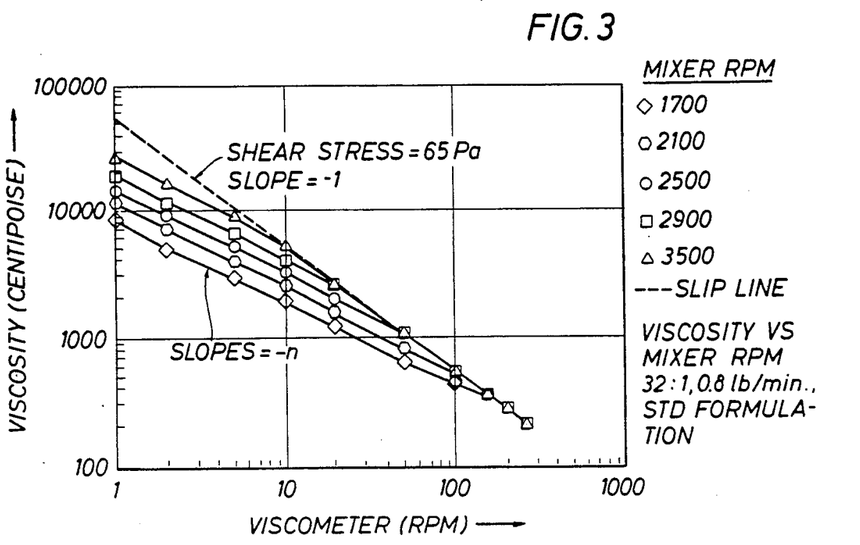
FIG. 3 is an example of viscosity data for a range of RPMs.
Figure 4A:
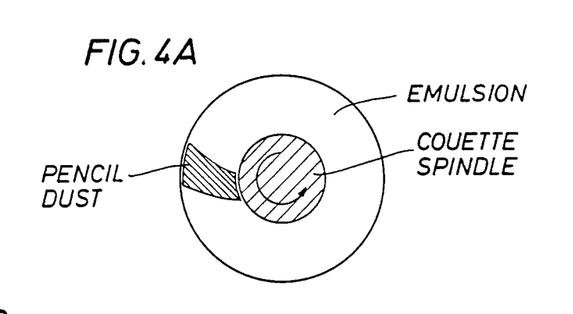
FIGS. 4A–4C show examples of yield stress, shearing, and slip in a couette viscometer.
Figure 4B:
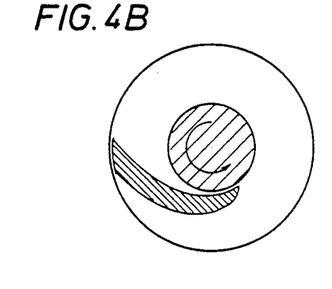
Figure 4C:
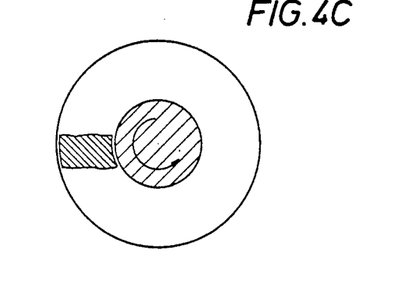

To determine the actual behavior of the subject emulsion, samples were taken at the output of the mixer and viscosity measurements were taken in a couette viscometer, Brookfield model DV3 with rotating spindles, spindles #21, #14 and #15 (solid shaft). A typical data set is shown in FIG. 3. To determine the significance of the slip line and the presence or absence of a significant yield stress, pencil dust was sprinkled on the emulsion across the annulus of the couette as shown in FIG. 4. Even at very low viscometer RPMs (0.1 RPM) the emulsion was observed to shear as shown in FIG. 4B, and the measured viscosity was consistent with the slopes shown in FIG. 3. It was concluded that the yield stress was insignificant since the pattern of FIG. 4A was not observed. At sufficiently high RPM (FIG. 4C), the emulsion slipped but did not shear, and a layer of water formed on top of the emulsion. This was due to coalescence at the surface of the spindle, producing a layer of free water, which rode up the spindle, perhaps driven by the expected rod-climbing behavior of the emulsion. It is believed that the spindle is oil-wet, and that the water forms on the oil film with a layer of surfactant between the oil and the water. The "slip line" of FIG. 3 corresponds to a shear stress of about 65 Pascals.

It was concluded that the emulsion can be adequately modeled as a power law fluid, provided that the shear stress is not too high, i.e. falls below the "slip line" of FIG. 3. The power law exponent, n, is about 0.3 for the standard formulation, and the viscosity and shear stress are given by $$\text{emulsion viscosity, } \mu_e = \dot{\gamma}^{n-1}\mu_0 \text{ Pascal-sec} \quad (5)$$

$$\text{shear stress, } \tau = \dot{\gamma}^n \mu_0 \text{ Pascals} \quad (6)$$

where n is approximately 0.35 and $\mu_0$ depends on the drop size, i.e. mixing conditions and surfactant properties.

To provide a check on the proper operation of the couette viscometer with the power law emulsion, measurements were taken with two different size (diameter) spindles and the shear was corrected for power law behavior. With a power law fluid, the shear at the spindle surface is given by (Krieger, I. M., "Shear Rate in the Couette Viscometer", Transactions of the Society of Rheology, Vol. 12, No. 1, pp 5-11, 1968)

$$\text{shear rate}, \dot{\gamma} = \frac{2}{n} \frac{1}{1 - \left(\frac{R_b}{R_c}\right)^{2/n}} \Omega \text{ sec}^{-1} \quad (7)$$

and the power law exponent n−1 is given by $$n - 1 = \frac{d(\ln \mu_e)}{d \ln(\Omega)} \quad (8)$$

Figure 5:
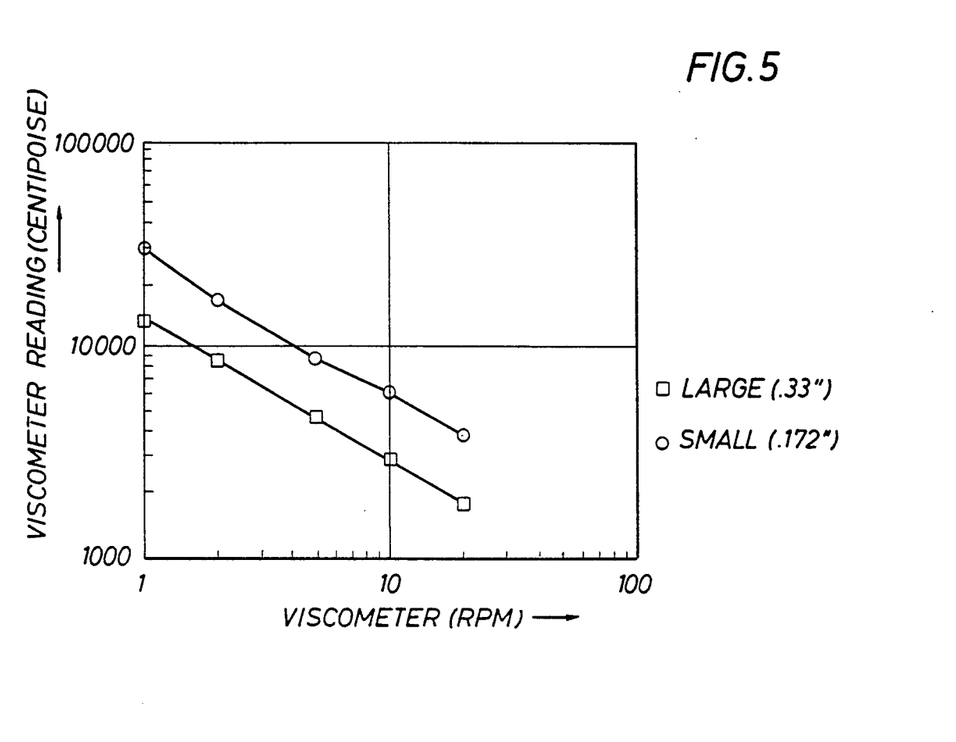
FIG. 5 is a graph of raw data for the two-spindle couette test.
Figure 6:
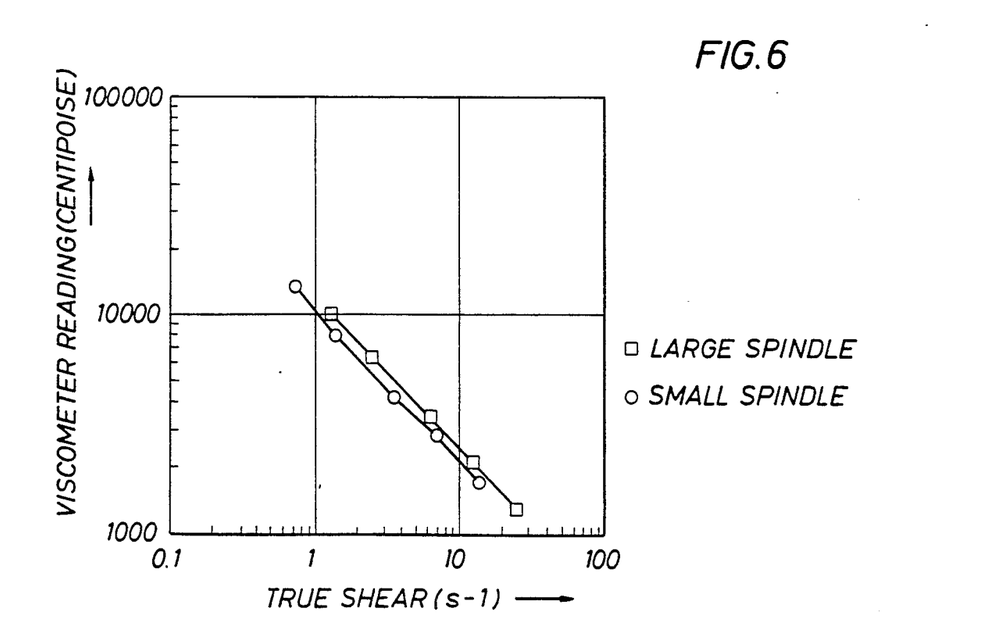
FIG. 6 is a graph of two-spindle data corrected for true shear.

In other words, no shear correction is required to obtain the correct slope from the plot of log (viscosity) vs log (RPM). Thus, the correct shear may be calculated by using the slope from the raw data without applying a correction for shear thinning. FIG. 5 shows a plot of the raw data for the two spindles, and FIG. 6 shows the corrected data plotting true shear vs. viscosity, using equation 6.

Measurement of HIPE Viscosity in a Capillary

Power Law Fluid Behavior in a Capillary

In a capillary, i.e. wherein flow is laminar, a power law fluid obeys the following equations for shear stress and pressure drop (Bird, R. B., Armstrong, R. C., Hassager, O., "Dynamics of Polymeric Fluids", Wiley, N.Y.):

$$\text{shear stress}, \tau = \left(Q_e \frac{\left(\frac{1}{n} + 3\right)}{\pi R^3}\right)^n \mu_0 \text{ Pascals} \quad (9)$$

and pressure drop per unit length in the capillary, $$\frac{dp}{dL} = \left(Q_e \frac{\left(\frac{1}{n} + 3\right)}{\pi R^3}\right)^n \frac{2\mu_0}{R} \text{ Pascal/meter} \quad (10)$$

The power law exponent n is given by the slope of $\log(dp/dL)$ vs $\log Q_e$ or $-\frac{1}{3}$ of the slope of $\log(dp/dL)$ vs $\log(R)$.

Measurement Configuration

It is desirable according to the process of the invention to make an in-line process measurement of viscosity by using two different tube diameters as shown in FIG. 7. Oil phase 10 and water phase 12 are withdrawn from their supplies by gear pumps 14, 16 and injected into pin mill mixer 30 via thermal flow meter 18, which may be a Rheotherm TU-⅛ for measuring oil phase flow, and mass flow meter 20, which may be a Micromotion DS-6, S-100 for measuring water phase flow. A differential pressure gauge 38 such as Honeywell Model ST-300 measures the pressure difference between the input to the mixer 30 and the output of the static mixer 32 which is mounted below the barrel cone of the mixer 30 to provide back pressure during start-up. Pressure gauge 38 is connected by means of fluid lines 39 and sealed by diaphragms S. The viscometer comprises lengths of tubing 40, 42 having different diameters. Inserted in each length of tubing, and spanning known distances, are differential pressure transmitters 44, 46 such as Honeywell Model ST-3000 connected to respective portions of the tubing 40, 42 by fluid lines 48, 50. Fluid lines 48, 50 are filled with e.g., silicone oil which is isolated from the emulsion by seals S. All pressure measurements are input to control system 70. The fluid lines for the pressure gauges should be as short as possible to reduce measurement errors.

It is highly desirable that the emulsion be maintained at a constant temperature during the measuring process. To this end, pin mill mixer 30 is equipped with a temperature control system and is surrounded by a heat exchanger 60 to establish the temperature. The tubing sections 40, 42 are wrapped in heater elements 62 to maintain the selected temperature. The heater element 62 may be wrapped with insulation (not shown) to further stabilize the temperature which is monitored by a thermocouple Tc and input to control system 70. Since the whole flow is going through both tube sections 40, 42, the total emulsion flow rate $Q_e$ is known from the flow meters 18, 20 on the feeds. The diameters of the tube sections 40, 42 are selected such that the pressure drop is in the range of about 5-50 inches of water, preferably about 50, and the diameter ratio is about 2:1. The two measurements of $$\frac{dp}{dL}$$

yields two equations (10) with two unknowns, $\mu_o$ and n, w can then be solved. The process is preferably automatically controlled by a control system 70 such as one including an Edge-Sweets control panel for an Edge-Sweets Flexamatic 2BT laboratory bench-top metering and dispensing process machine. Control system 70 includes a computer which can solve equation (10) for the values, $\mu_o$ and n, for display.

Figure 8:
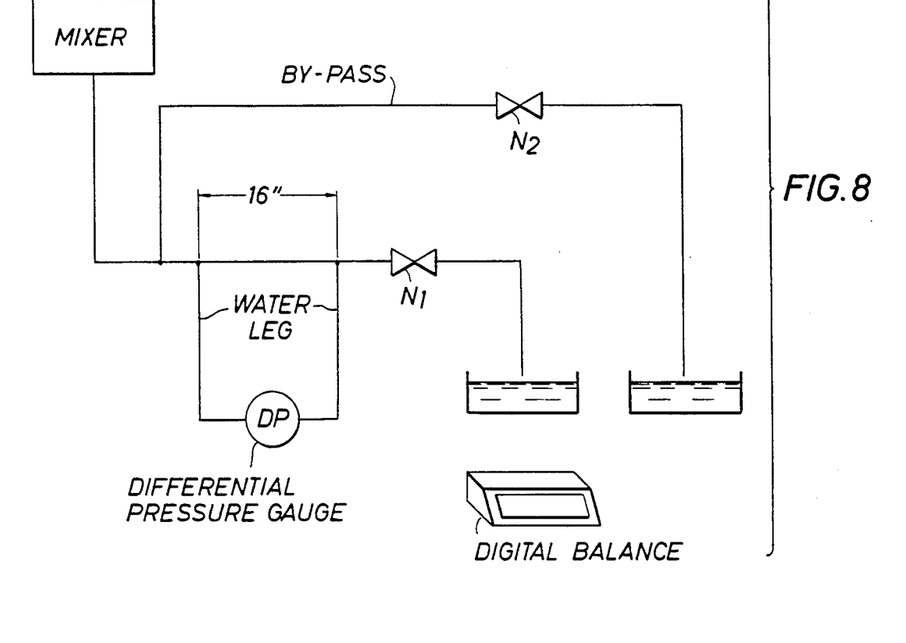
FIG. 8 is a schematic for an "in-line" capillary viscometer used for experiments.
Figure 9:
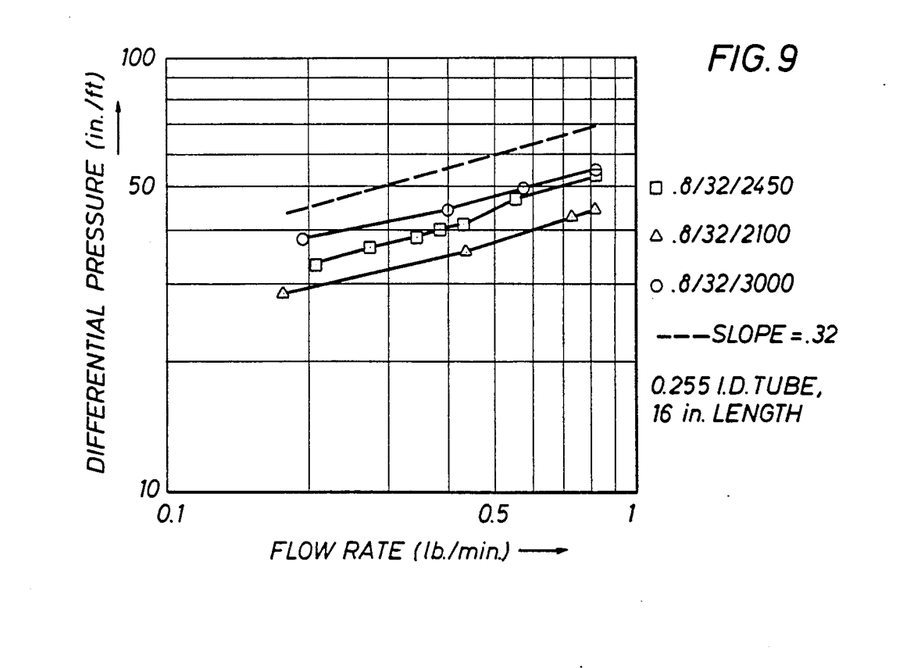
FIG. 9 is a graph of data from capillary viscometer measurements taken using the test set-up of FIG. 8.

For purposes of making laboratory measurements, however, more values of flow rate can be taken by varying the flow rate directly by means of the test set-up with a by-pass line as shown in FIG. 8. This was done with two needle valves $N_1$ and $N_2$, and the flow rate through the capillary and $N_1$ was measured by weighing the emulsion collected on a digital balance over a two minute time period. The supply and metering equipment has been deleted for clarity. Graphs of the resulting measurements are shown in FIG. 9. The slope is about what is expected from the couette measurements. The level is seen to vary with RPM, flow rate and water/oil ratio. One set of measurements was taken from high to low flow rates and then back to high to show the repeatability of the measurement. A Honeywell smart differential pressure transmitter model ST3000 with a resolution of 0.01 inches of water was used. Actual measured pressure drops were as high as 55 inches of water. In this laboratory procedure, the pressure transmitter diaphragm was isolated from the emulsion by simply filling the connecting tubing with water. The flow tubing inside diameter was 0.255 inches. In a controlled process measurement, such as in FIG. 7, a remote diaphragm seal, S, such as those manufactured by Rosemount, Inc., is preferably used to isolate the transmitter from the process. This device presents a flush, sealed diaphragm to the flow line and transmits the pressure to the meters through flexible tubes 48, 50 filled with silicone oil.

Effect of Slip Layers

Figure 10:
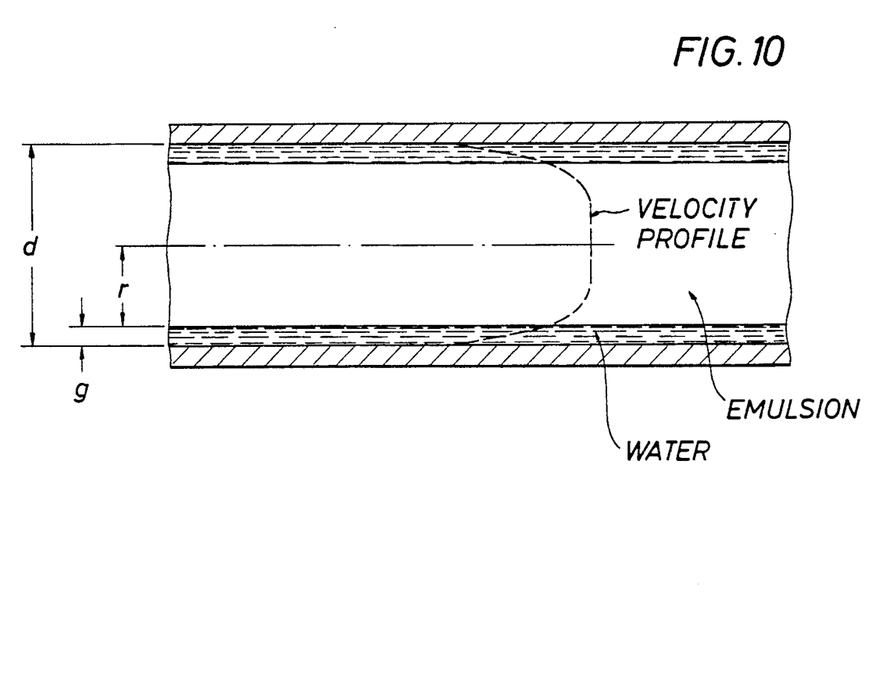
FIG. 10 is a schematic diagram showing two component capillary flow.

Excess water may be produced in the mixer. This causes a slip layer g to form in the capillary as shown in FIG. 10. Most of the pressure drop takes place in the slip layer, and the pressure drop is greatly reduced relative to slip-free emulsion. If a slip layer g is present, the velocity at a given radial position r in the slip layer is given by (Giedt, W. H., "Principles of Engineering Heat Transfer", Van Nostrand, N.Y., 1957)

water film velocity, $$u_w(r) = \frac{dp}{dL} \frac{1}{4\mu_w}\left(\frac{d^2}{4} - r^2\right) \text{meters/sec} \quad (11)$$

and in the emulsion by (Bird et. al.)

emulsion velocity, $$u_e(r) = \frac{Q_e}{\pi r^2} - \frac{r}{\frac{1}{n}+3}\left(\frac{dp}{dL} \frac{r}{2\mu_0}\right)^{1/n} \text{meters/sec} \quad (12)$$

Figure 11:
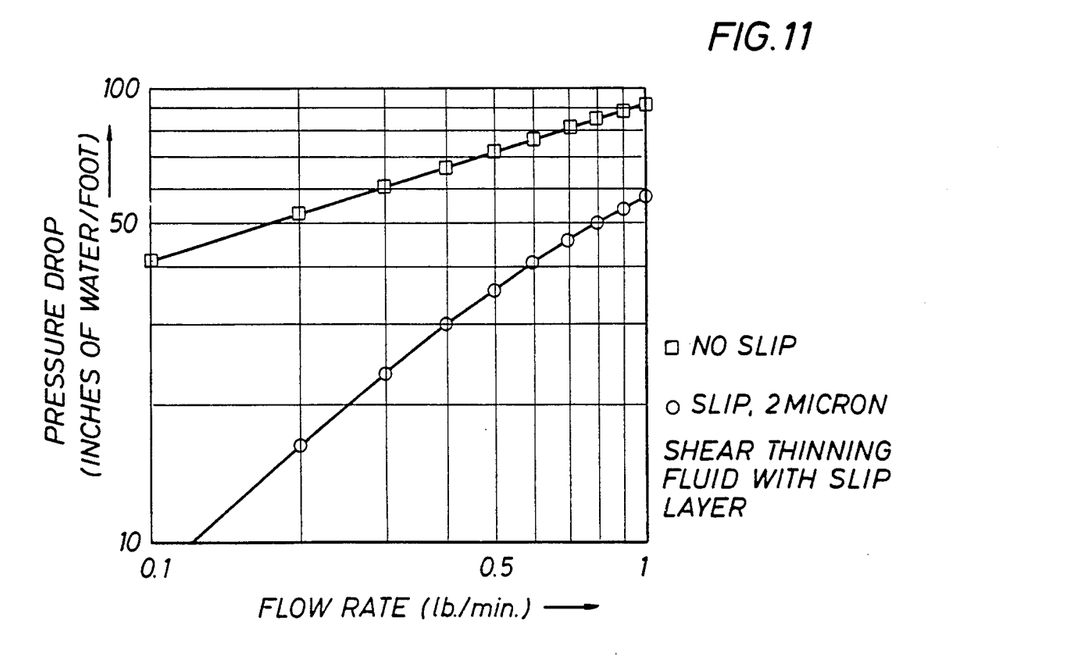
FIG. 11 is a graph showing calculated capillary pressure drop vs. flow rate with and without a slip layer.
Figure 12:
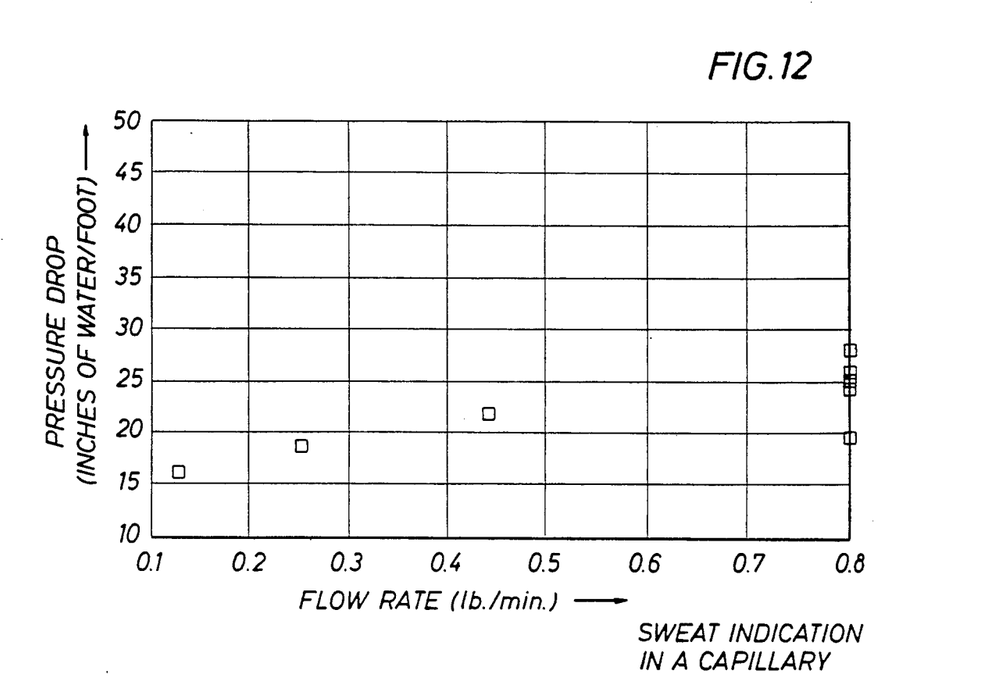
FIG. 12 is a plot of data showing sweat indication in a capillary.

By equating these velocities at the water/emulsion interface, the pressure drop can be obtained as a function of slip layer thickness. FIG. 11 shows graphs of the calculated pressure drops for slip-free emulsion and in the presence of a two micron water layer using the emulsion parameters obtained from the couette viscometer. Even a small amount of slip results in a lower pressure drop and steeper slope (the slope for a Newtonian fluid is one). FIG. 12 shows data taken at a low (below 2000) mixer RPM. As the flow rate was raised to 0.8 lb/min., a slip layer developed, as shown by the pressure drop fluctuation indicated by the five successive pressure drop readings plotted in the figure. Thus, viscosity or head pressure is a sensitive indicator of the presence of slip, which in turn may indicate a change in the surfactant.

Correlation of Capillary Pressure Drop With Head Pressure

Figure 13:
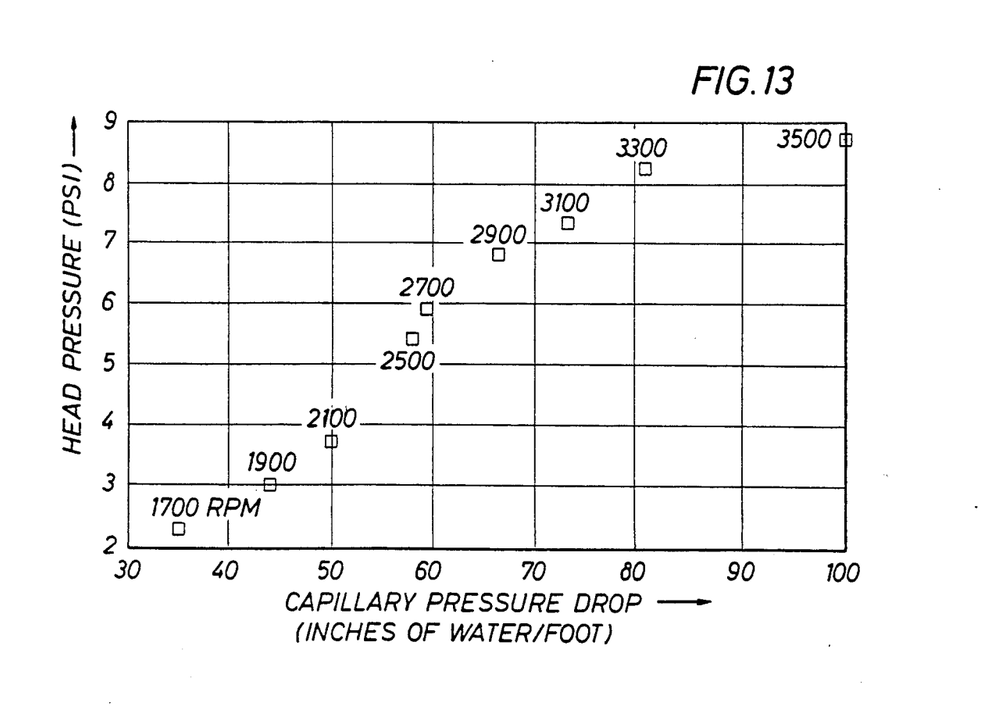
FIG. 13 is a plot of data showing correlation between capillary pressure drop and head pressure.

FIG. 13 shows head pressure vs capillary pressure drop over a range of 1700 to 3500 RPM.

The head pressure correlates well with the pressure drop and may serve as an acceptable process quality indicator. It has the advantage of being simpler to implement than viscosity. The advantage of viscosity over head pressure is that (1) viscosity can give two independent parameters (level and slope) (2) viscosity is intrinsic to the material and not dependent upon the specific mix head, and so may be more useful for development work, and not subject to variation with head wear or emulsion build-up. There is some evidence that the emulsion buildup in the mix head can vary, causing head pressure variations but no changes in emulsion properties. Pressure drop measurements downstream of the mix head would not be subject to these types of variations.

While the invention has been described with respect to an emulsion, it will be appreciated that the invention is applicable in any process where the fluid product is a power law fluid.

What is claimed is:

1. A process for the preparation of a porous cross-linked polymeric material comprising the steps of:
    (a) providing a water phase comprising water and an electrolyte;
    (b) providing an oil phase comprising a mixture of polymerizable monomers comprising at least one vinyl monomer and a crosslinker;
    (c) providing a surfactant to the water phase, the oil phase, or both the water and the oil phases;
    (d) combining and mixing said water phase and said oil phase in a mixer under conditions effective to produce an emulsion having at least 90 weight percent, based on the emulsion, of water as the internal phase;
    (e) providing a capillary for receiving the emulsion output of said mixer, said capillary having segments of different diameters;
    (f) maintaining said emulsion at a preselected temperature as it flows through said capillary to a capillary output;
    (g) measuring the pressure drop across selected lengths of each of said different diameter segments;
    (h) utilizing the pressure drop to adjust operating conditions to produce a porous cross-linked polymeric material;
    (i) adding to at least a portion of said oil phase, water phase or emulsion, an effective amount of a polymerization catalyst to cure the polymerizable monomers;
    (j) polymerizing said emulsion from said capillary output under conditions effective to cure the polymerizable monomers; and
    (k) removing at least a portion of the water from said cured emulsion.

2. The process of claim 1 wherein further including the steps of measuring the flow rate of said emulsion through said capillary and calculating the power law viscosity parameters $\mu_e$ and n of said emulsion using the equation $$\frac{dp}{dL} = \left(Q_e \frac{\left(\frac{1}{n}+3\right)}{\pi R^3}\right)^n \frac{2\mu_0}{R} \text{ Pascal/meter}$$

where $\frac{dp}{dL}$ is the pressure drop per unit length of capillary in Pascal/meter,
$Q_e$ is the emulsion volume flow rate in meter$^3$/sec,
n is the power law exponent,
R is the capillary radius in meters,
and
$\mu_o$ is the emulsion viscosity at a shear of 1/sec in Pascal-sec.

3. The process of claim 2 further including the step of measuring the pressure drop across said mixer.

4. The process of claim 3 further including the step of periodically repeating said measurements and calculations over a period of time.

5. The process of claim 4 further including the steps of:
- plotting said mixer pressure versus time over said period of time;
- plotting said calculated viscosity versus time over said period of time; and
- comparing said plots to determine the condition of said mixer.

6. The process of claim 4 further including the steps of:
- plotting said mixer pressure versus time over said period of time;
- plotting said pressure drop across one of said capillaries versus time over said period of time; and
- comparing said plots to determine a characteristic of said emulsion.

7. The process of claim 4 further including the steps of:
- plotting said mixer pressure versus time over said time period;
- plotting said pressure drop across one of said capillaries versus time over said time period; and
- comparing said plots to determine the condition of said mixer.

8. The process of claim 3 further including the step of determining the presence or absence of sweat from said mixer pressure measurement 9. The method of claim 1 wherein said operating conditions in step (h) is adjusted by adjusting the viscosity of said emulsion.

10. The method of claim 1 wherein said operating conditions in step (h) is adjusted by adjusting steps (a), (b), (c), (d) and/or (i).

* * * * *